United States Patent [19]

Watanabe et al.

[11] Patent Number: 4,658,042

[45] Date of Patent: Apr. 14, 1987

[54] PROCESS FOR THE PREPARATION OF MALEIC ANHYDRIDE

[75] Inventors: Tokisuke Watanabe; Shinji Kitaoka; Yoshio Suwa, all of Kurashiki, Japan

[73] Assignee: Mitsubishi Gas Chemical Company, Inc., Tokyo, Japan

[21] Appl. No.: 752,914

[22] Filed: Jul. 8, 1985

[30] Foreign Application Priority Data

Jul. 16, 1984 [JP] Japan .................................. 59-147078

[51] Int. Cl.$^4$ ............................................. C07D 307/60
[52] U.S. Cl. .................................... 549/257; 549/256; 549/262
[58] Field of Search .......................... 549/256, 257, 262

[56] References Cited

U.S. PATENT DOCUMENTS

| | | | |
|---|---|---|---|
| 1,914,556 | 6/1933 | Conover | 562/593 |
| 3,642,829 | 2/1972 | Weyens | 549/262 |
| 4,260,546 | 4/1981 | Schroeder et al. | 549/262 |

*Primary Examiner*—Henry R. Jiles
*Assistant Examiner*—Bernard I. Dentz
*Attorney, Agent, or Firm*—Frishauf, Holtz, Goodman & Woodward

[57] ABSTRACT

In the production of maleic anhydride, scale formation in an evaporator and pipes is a very difficult problem. By the process disclosed herein, scale formation in a maleic anhydride preparation apparatus can satisfactorily be prevented, and therefore, maleic anhydride preparation apparatus can be operated continuously for a long period. Further, it is also possible to significantly reduce the formation of fumaric acid. The process is that when conducting the concentration and dehydration of an aqueous solution of maleic acid, a small amount of hydrogen peroxide is added to the aqueous solution. Scale is formed by condensation of phenols and aldehydes, and quinones and aldehydes. Hydrogen peroxide added acts to oxidize aldehydes contained in the aqueous solution.

11 Claims, No Drawings

PROCESS FOR THE PREPARATION OF MALEIC ANHYDRIDE

BACKGROUND OF THE INVENTION

1. Field of the Invention

The present invention relates to a process for the preparation of maleic anhydride, and more particularly to a process for preventing the formation of scales in apparatus during concentration and dehydration operations of an aqueous solution of maleic acid.

2. Description of the Prior Arts

Maleic anhydride has been generally prepared by concentration and dehydration of an aqueous solution of maleic acid, which is obtained by absorbing in water, in an apparatus such as a scrubber, a gas containing maleic anhydride, formed by catalytic oxidation of benzene, or gaseous by-products containing maleic anhydride, formed during the production of phthalic anhydride by catalytic oxidation of o-xylene or naphthalene.

The concentration and dehydration operations described above are performed by concentration and dehydration of an aqueous solution of maleic acid within a short period of time in apparatus such as a rotary film evaporator and a falling film evaporator, the water contained in the charged aqueous solution and the water formed by the dehydration reaction are evaporated, and maleic anhydride which is formed in the liquid phase is recovered in a molten state, or maleic anhydride is evaporated with the said water and the vapor mixture containing water and maleic anhydride is cooled to a temperature which does not allow water to condense and only maleic anhydride is separated and recovered in pure form (Japanese Patent Disclosure Nos. 80816/1976 and 50316/1975).

A variety of by-products are formed by the above-described processes for the preparation of maleic anhydride, and when an aqueous solution of maleic acid containing such by-products is processed as described above, there takes place accumulation of high-boiling point products such as resinous, tarry or gelatinous substances on the inner walls of the concentration-dehydration apparatus or pipes, and they tend to clog the apparatus and pipes.

In order to overcome these deficiencies, Japanese Patent Disclosure No. 80816/1976 discloses a process for the preparation of maleic anhydride in which the molten maleic anhydride obtained and discharged from a rotary film evaporator is circulated into a funnel-shaped discharging section provided at the lower part of the evaporator, through a nozzle which is positioned at about tangential direction to the wall of the discharging section. Japanese Patent Disclosure No. 50316/1975 (corresponds to British Patent Application No. 40528/1973) adopts a process in which the concentrated liquid is taken out from a distillation-dehydration vessel, the concentrated liquid is filtered to remove the insoluble resinous residue, and the filtrate is circulated to the first scrubber of the process.

SUMMARY OF THE INVENTION

1. Objects of this Invention

These processes mentioned above, however, cannot be regarded as perfect solutions of the problem, and should be improved further.

Once the high-boiling point products mentioned hereinbefore are formed and deposited on the inner wall of the evaporator, maleic acid impregnates into or adheres on the deposit, resulting in a rapid formation of fumaric acid. This causes not only a reduced heat transfer but also formation of stiff scales. This brings about an overload on the rotor of a rotary film evaporator, and its operation has to be stopped.

That is, by the process disclosed in Japanese Patent Disclosure No. 50316/1975, i.e. a process which comprises mixing a concentrated liquid obtained from distillation-dehydration vessel with water, filtering an aqueous suspension thus formed to separate resinous materials and fumaric acid from the aqueous suspension, and recycling the filtrate to the first scrubber of the process, or Japanese Patent Disclosure No. 80816/1976, i.e. a process which comprises washing the funnel-shaped discharging section of a rotary film evaporator with molten maleic anhydride by recycling a part of molten maleic anhydride discharged from the section to a nozzle which is specially designed and positioned, it is impossible to remove resinous scale once formed and deposited on the inner wall surfaces of maleic anhydride preparation apparatus. Therefore, by the use of either one of the two processes mentioned above, continuous operations of a film evaporator, especially a rotary film evaporator, are still difficult. Accordingly, a complete means for preventing the formation of scale in a maleic anhydride preparation apparatus, allowing continuous operations of a rotary film evaporator and suppressing the formation of fumaric acid, is to prevent the formation of resinous materials per se, in the maleic anhydride preparation apparatus.

We have made intensive studies on process to suppress the formation of such high-boiling point products, wich cause the clogging of the apparatus during the concentration and dehydration operations, and found a simple process for preventing the formation of resinous materials and thus completed the present invention.

Accordingly, an object of this invention is to provide a process for the preparation of maleic anhydride which allows a continuous operation for a long time. The second object of this invention is to provide a simple process for preventing the formation of scale in a maleic anhydride preparation apparatus. The third object of this invention is to provide a process for preventing the clogging of a maleic anhydride preparation apparatus without recycling process streams, thereby saving the necessary utilities. Other more specific objects will in part be obvious and will in part appear hereinafter.

2. Findings leading to this Invention

The aqueous solution of maleic acid described above contains a variety of impurities, and a detailed investigation on the impurities showed thart the solution contains several aldehydes such as formaldehyde, phenols such as phenol, cresol, hydroquinone, and xylenol, quinones such as benzoquinone, and other impurities.

It is considered that the formation of such impurities as reaction intermediates or by-products cannot be prevented whatever hydrocarbons are used as the starting materials, and that it is difficult to completely prevent their formation by attempts such as improvement of the reaction catalysts. It was found that when an aqueous solution of maleic acid containing such impurities is heated, concentrated, and dehydrated as it is, there takes place the formation of resinous substances from the said impurities for the reason of such as condensation reaction of phenols and aldehydes or of quinones and aldehydes, and it induces the clogging of the apparatus. We have found that when conducting the concentration and dehydration of the aqueous solution containing maleic acid, if hydrogen peroxide is added to the aqueous solution, the formation of the resinous or gelatinous materials can effectively be avoided.

3. Gist of this Invention

The present invention was realized based on these findings, and the gist thereof is a process for the preparation of maleic anhydride by concentration and dehydration of an aqueous solution containing maleic acid which is obtained by absorbing in water the gaseous reaction products formed by catalytic oxidation of benzene, or by absorbing in water the spent gas from the production of phthalic anhydride formed by catalytic oxidation of o-xylene or naphthalene, characterized in that when conducting the concentration and the dehydration operations, hydrogen peroxide is added to the said aqueous solution containing maleic acid.

DETAILED DESCRIPTION OF THE INVENTION

The present invention can be applied widely to aqueous solutions containing maleic acid in a concentration of from 20 wt% to 60 wt%, for example, an aqueous solution containing maleic acid which is obtained by dissolving in water the gaseous reaction product formed by vapor phase oxidation of benzene in the presence of a catalyst comprising vanadium pentoxide and phosphorus pentoxide as the main components; an aqueous solution containing by-produced maleic acid which is obtained by dissolving in water the spent gas after separation of phthalic anhydride from the gaseous products which are formed by vapor phase oxidation of o-xylene or naphthalene over a catalyst comprising vanadium pentoxide as the main component; or other such solutions.

In the aqueous solution containing maleic acid described above, an aqueous solution containing maleic acid in a relatively low concentration of 20–30 wt% is preferably preheated to 40°–50° C., sent to a falling film evaporator, concentrated to a maleic acid concentration of 40–60 wt% by evaporation at 60°–70° C., and then sent to a rotary film evaporator. When an aqueous solution with a high concentration, i.e. concentration of higher than 40 wt%, of maleic acid is available, it may be charged directly to a rotary film evaporator.

In the present invention, rotary film evaporator means the evaporator wherein rotary disc is rotated and the liquid to be treated is forced to form a film on the heating surface of the evaporator by its centrifugal force and is vaporized.

Falling film evaporator means the evaporator wherein the liquid to be treated falls down along the heating surface of the evaporator and the vaporized gas and liquid are drawn out downwards.

In the process of the present invention, when conducting the concentration and the dehydration operations, hydrogen peroxide is added to the aqueous solution. Hydrogen peroxide may be added to the aqueous solution of maleic acid before preheating, after preheating, in a falling film evaporator, or before transfer to a rotary film evaporator, but in order to avoid a too vigorous reaction, it is preferable to add it when the temperature of the aqueous solution is within a range of 0°–100° C., and more preferably from ambient temperature to 50° C.

It is sufficient to add hydrogen peroxide in an amount which is required to oxidize the aldehydes in the aqueous solution containing maleic acid, and a smaller amount is also effective. Generally, 0.5–10 g, preferably 0.5–7 g, of hydrogen peroxide (calculated as $H_2O_2$, i.e. 100% hydrogen peroxide) per 1 liter of the aqueous solution is satisfactory, and the addition of an excess of hydrogen peroxide may preferably be avoided because it is not only uneconomical but it also decomposes maleic acid. It is preferable that hydrogen peroxide is added in a form of aqueous solution.

The rotary film evaporator is operated at a temperature of 140°–160° C., and after complete evaporation of water and dehydration, the resulting molten maleic anhydride is drawn out.

In accordance with the process of the present invention, by addition of hydrogen peroxide to an aqueous solution containing maleic acid, the formation of resinous or tarry materials can be greatly reduced, clogging of the apparatus and pipes can be prevented, and it allows a continuous operation over a long period. At the same time, since maleic acid cannot impregnate into or adhere on the scale, it is also effective in preventing the conversion of maleic acid to fumaric acid, and maleic anhydride with a high purity can be obtained.

In the following, the present invention will be materially explained by showing experimental data.

EXAMPLE 1

One hundred grams of aqueous solutions of maleic acid (maleic acid content: 28 wt% or 50 wt%), which were obtained by absorbing in water gaseous reaction products, formed by catalytic oxidation of benzene or a spent gas from the production of phthalic anhydride formed by catalytic oxidation of o-xylene, were placed in 300 ml glass Erlenmeyer flasks equipped with a reflux condenser, respectively, and the solutions were heated under reflux for 4 hr. After cooling, the amounts (mg/100 g of aqueous solution) of resinous or gelatinous materials formed were determined.

Apart from them, formaldehyde and various kinds of phenols or p-benzoquinone were added, in the amounts shown in Table 1, to 100 g of 30 wt% aqueous solutions of maleic acid which were prepared by dissolving commercial maleic acid (purity: higher than 99.9 wt%) in pure water. The solutions thus prepared were heated under reflux under identical conditions as described above, and the amounts (mg/100 g) of resinous or genatinous materials formed were determined. The results are shown in Table 1.

TABLE 1

| | | The amount of resinous or gelous materials formed (mg/100 g) | | | | |
|---|---|---|---|---|---|---|
| | | Composition of aqueous solution of maleic acid | | | | |
| | | Phenols.quinones | | | Maleic | Resinous.gelous |
| Kind of samples | Run No. | Name | Amount (wt %) | Formaldehyde (wt %) | acid (wt %) | materials formed (mg/100 g) |
| Aqueous solution obtained from a catalytic oxidation of hydrocarbons | | | | | | |

TABLE 1-continued

The amount of resinous or gelous materials formed (mg/100 g)

| | | Composition of aqueous solution of maleic acid | | | | Resinous.gelous materials formed (mg/100 g) |
|---|---|---|---|---|---|---|
| | | Phenols.quinones | | | Maleic | |
| Kind of samples | Run No. | Name | Amount (wt %) | Formaldehyde (wt %) | acid (wt %) | |
| Oxidation of benzene | 1 | Phenol | 0.03 | 0.30* | 28 | 100 |
| | 2 | Phenol | 0.05 | 0.50* | 50 | 170 |
| Oxidation of o-xylene | 3 | Phenol | 0.04 | 0.30* | 28 | 100 |
| | | Hydroquinone | 0.015 | | | |
| | 4 | Phenol | 0.07 | 0.45* | 50 | 160 |
| | | Hydroquinone | 0.027 | | | |
| Aqueous solutions prepared by mixing pure chemicals | 5 | Not added | 0 | 0 | 30 | 0 |
| | 6 | Not added | 0 | 0.37 | 30 | 0 |
| | 7 | Phenol | 0.2 | 0 | 30 | 0 |
| | 8 | Phenol | 0.2 | 0.37 | 30 | 150 |
| | 9 | Hydroquinone | 0.2 | 0.37 | 30 | 210 |
| | 10 | Cresol | 0.2 | 0.37 | 30 | 150 |
| | 11 | Xylenol | 0.2 | 0.37 | 30 | 150 |
| | 12 | p-benzoquinone | 0.2 | 0.37 | 30 | 100 |

*Quantity of aldehydes was determined and re-calculated it as formaldehyde.

The resinous or gelous materials which were formed from phenol, hydroquinone, or p-benzoquinone by the reactions in Example 1 described above were practically insoluble not only in hot water but also in solvents such as acetone, benzene, xylene, chloroform, and pyridine, and were insoluble in molten maleic anhydride at 150° C. Incidentally, the resinous or gelatinous materials which were formed from cresol or xylenol were insoluble in hot water, but soluble in solvents such as acetone. These resinous or gelous materials showed considerable adhesiveness, and it may be readily presumed that once resinous materials are formed in and deposited on the apparatus, they will cause to bring scales by a rapid formation of fumaric acid and will result cloggings of apparatuses and pipes.

The runs shown in Example 1 described above were shown for the purpose to demonstrate why resinous or gelatinous materials are formed in the apparatus in conventional process widely used.

EXAMPLE 2

Into 100 g each of the aqueous solutions used in Example 1, 0.3 g of hydrogen peroxide (calculated as 100% hydrogen peroxide) was added respectively at ambient temperature, and the aqueous solutions modified with hydrogen peroxide were heated under reflux under the exactly same conditions used in Example 1. The results arre shown in Table 2.

TABLE 2

Effect of hydrogen peroxide addition for suppressing formation of resinous or gelous materials

| | | Composition of aqueous solution of maleic acid | | | | | Resinous.gelous materials formed (mg/100 g) |
|---|---|---|---|---|---|---|---|
| | | Phenols.quinones | | | Maleic | Hydrogen | |
| Kind of samples | Run No. | Name | Amount (wt %) | Formaldehyde (wt %) | acid (wt %) | peroxide (wt %) | |
| Aqueous solution obtained from a catalytic oxidation of hydrocarbons | | | | | | | |
| Oxidation of benzene | 13 | Phenol | 0.03 | 0.30* | 28 | 0.3 | 0 |
| | 14 | Phenol | 0.05 | 0.50* | 50 | 0.3 | 0 |
| Oxidation of o-xylene | 15 | Phenol | 0.04 | 0.30* | 28 | 0.3 | 0 |
| | | Hydroquinone | 0.015 | | | | |
| | 16 | Phenol | 0.07 | 0.45* | 50 | 0.3 | 0 |
| | | Hydroquinone | 0.027 | 0.45* | 50 | 0.3 | 0 |
| Aqueous solution prepared by mixing pure chemicals | 17 | Phenol | 0.2 | 0.37 | 30 | 0.3 | 0 |
| | 18 | Hydroquinone | 0.2 | 0.37 | 30 | 0.3 | 0 |
| | 19 | Cresol | 0.2 | 0.37 | 30 | 0.3 | 0 |
| | 20 | Xylenol | 0.2 | 0.37 | 30 | 0.3 | 0 |
| | 21 | p-benzoquinone | 0.2 | 0.37 | 30 | 0.3 | 0 |

*Quantity of aldehydes was determined and re-calculated it as formaldehyde.

The runs shown in Example 2 described above were shown for the purpose to demonstrate the fact that if hydrogen peroxide is added to the aqueous solutions in accordance with the process of this invention, the resinous or gelatinous materials are not formed.

EXAMPLE 3

When conducting the concentration of aqueous solutions of maleic acid (maleic acid content: 28 wt%), which were obtained by absorbing in water gaseous reaction products, formed by catalytic oxidation of benzene or a spent gas from the production of phthalic anhydride formed by catalytic oxidation of o-xylene, at charge rates of 3.3 m³/hr in a falling film evaporator at a temperature of 70° C. and further conducting the concentration and dehydration of the preconcentrated aqueous solutions in a rotary film evaporator at a temperature of 140°–150° C., 35 wt% aqueous solution of hydrogen peroxide was continuously added at a rate of 28 liter/hr to the aqueous solutions at ambient temperature. In these cases, even after seven days continuous operations, formation of resinous or gelatinous materials was not observed at all during the concentration and dehydration operations, and formation of only a trace amount of fumaric acid was observed.

Further, when conducting the concentration and dehydration of the same aqueous solutions of maleic acid used in the above, except that maleic acid contents are 50 wt%, at charge rates of 1.75 m³/hr in a rotary film evaporator at a temperature of 140°–150° C., 35 wt% aqueous solution of hydrogen peroxide was continuously added at a rate of 28 liter/hr to the aqueous solutions at ambient temperature. The results observed were essentially the same as those of the above.

It is a significant improvement that although the operations by the conventional processes require removal of scales in the apparatus every two or three days, inspection of the inner parts of the apparatus after a seven days continuous operation according to Example 3 which is an embodiment of this invention showed that they were kept clean without any evidence of the deposition of scales. Example 3 described above clearly shows that by the process of this invention, a continuous operation over a long period can be conducted.

We claim:

1. A process for the preparation of molten maleic anhydride by complete evaporation of water and dehydration within a rotary film evaporator of an aqueous solution containing maleic acid which is obtained by absorbing in water the gaseous reaction products formed by catalytic oxidation of benzene, or by absorbing in water the spent gas from the production of phthalic anhydride formed by catalytic oxidation of o-xylene or naphthalene, characterized in that when or prior to conducting the evaporation and the dehydration operations, hydrogen peroxide is added to said aqueous solution containing maleic acid to prevent the formation of resinous or gelatinous substances that would otherwise accumulate within the rotary film evaporator, and the amount of hydrogen peroxide added is from 0.5 g to 10 g calculated as $H_2O_2$ per 1 liter of said aqueous solution.

2. The process as claimed in claim 1 wherein the amount of hydrogen peroxide added is within a range of from 0.5 g to 7 g calculated as $H_2O_2$ per 1 liter of said aqueous solution containing maleic acid.

3. The process as claimed in claim 1 wherein hydrogen peroxide is added to said aqueous solution containing maleic acid at a temperature of from 0° C. to 100° C.

4. The process as claimed in claim 3 wherein hydrogen peroxide is added to said aqueous solution containing maleic acid at a temperature of from ambient temperature to 50° C.

5. The process as claimed in claim 1 wherein hydrogen peroxide is added in a form of an aqueous solution of hydrogen peroxide.

6. The process as claimed in claim 5 wherein the amount of hydrogen peroxide added is within a range of from 0.5 g to 10 g calculated as $H_2O_2$ per 1 liter of said aqueous solution containing maleic acid and the aqueous solution of hydrogen peroxide is added to the aqueous solution containing maleic acid at a temperature of from 0° C. to 100° C.

7. The process as claimed in claim 6 wherein the temperature is within a range of from ambient temperature to 50° C.

8. The process as claimed in claim 7 wherein the addition amount is within a range of from 0.5 g to 7 g calculated as $H_2O_2$ per 1 liter of said aqueous solution containing maleic acid.

9. The process as claimed in claim 6 wherein the addition amount is within a range of from 0.5 g to 7 g calculated as $H_2O_2$ per 1 liter of said aqueous solution containing maleic acid.

10. The process as claimed in claim 1 wherein the rotary film evaporator is operated at a temperature of 140° C. to 160° C.

11. The process as claimed in claim 9 wherein the rotary film evaporator is operated at a temperature of 140° C. to 160° C.

* * * * *